US012697131B1

(12) United States Patent

Wolek

(10) Patent No.: US 12,697,131 B1

(45) Date of Patent: Aug. 4, 2026

(54) RETINACULATOME AND A METHOD OF TRANSECTING A FLEXOR RETINACULUM IN A CARPAL TUNNEL RELEASE SURGERY USING THE RETINACULATOME

(71) Applicant: 100424194 Ontario Inc., Pickering (CA)

(72) Inventor: Ryan Wolek, Pickering (CA)

(73) Assignee: 1000424194 Ontario Inc., Pickering (CA)

( * ) Notice: Subject to any disclaimer, the term of this patent is extended or adjusted under 35 U.S.C. 154(b) by 0 days.

(21) Appl. No.: 19/422,063

(22) Filed: Dec. 16, 2025

(51) Int. Cl.
| | |
|---|---|
| *A61B 17/32* | (2006.01) |
| *A61B 17/00* | (2006.01) |
| *A61B 17/02* | (2006.01) |
| *A61B 90/00* | (2016.01) |

(52) U.S. Cl.
CPC .... *A61B 17/320036* (2013.01); *A61B 90/361* (2016.02); *A61B 2017/320052* (2013.01); *A61B 2017/320056* (2013.01)

(58) Field of Classification Search
CPC ........ A61B 17/3211; A61B 17/320016; A61B 17/320036; A61B 2017/32004; A61B 2017/320052; A61B 2017/320056; A61B 90/361
See application file for complete search history.

(56) References Cited

U.S. PATENT DOCUMENTS

| | | | |
|---|---|---|---|
| 4,962,770 A | 10/1990 | Agee et al. | |
| 4,963,147 A * | 10/1990 | Agee .............. A61B 17/320036 | |
| | | | 606/170 |
| 5,323,765 A | 6/1994 | Brown | |
| 5,431,153 A | 7/1995 | Lee | |
| 5,908,433 A * | 6/1999 | Eager ..................... A61B 90/30 | |
| | | | 606/170 |

(Continued)

FOREIGN PATENT DOCUMENTS

| | | |
|---|---|---|
| WO | 2017087000 A1 | 5/2017 |
| WO | 2020076307 A1 | 4/2020 |
| WO | 2023028560 A1 | 3/2023 |

OTHER PUBLICATIONS

Arthrex; NanoScopic™ Release System; Endoscopic Carpal Tunnel Release Surgical Technique Guide; arthrex.com; Mar. 2023 Arthrex, Inc.

(Continued)

*Primary Examiner* — Tuan V Nguyen

(57) ABSTRACT

A retinaculatome and a method of transecting a flexor retinaculum in a carpal tunnel release surgery using the retinaculatome are provided. The method may include inserting a borescope into a sleeve interior cavity of a sterile borescope sleeve of the retinaculatome. The sterile borescope sleeve may include a sleeve exterior shell that is sealed along its length and at a sleeve distal end. The sleeve distal end may have an incision imaging window transparent to the sleeve interior cavity. The method may further include positioning a surgical blade in a mounted blade position defined by a surgical blade mount connected to a lower guide plate extending from the sleeve distal end. The method may further include positioning the retinaculatome within a surgical incision; and transecting the flexor retinaculum by advancing the surgical blade while viewing through the incision imaging window using the borescope.

20 Claims, 9 Drawing Sheets

(56) References Cited

U.S. PATENT DOCUMENTS

| | | | |
|---|---|---|---|
| 6,019,774 | A | 2/2000 | Weiss et al. |
| 6,685,717 | B1 | 2/2004 | Ilic |
| 9,968,240 | B2 | 5/2018 | Agee et al. |
| 10,245,062 | B2 | 4/2019 | Seymour |
| 11,529,162 | B2 | 12/2022 | DaSilva |
| 12,318,106 | B2 | 6/2025 | Bright et al. |
| 2011/0046652 | A1 | 2/2011 | Rehnke et al. |
| 2014/0031621 | A1* | 1/2014 | Liu ........................ A61B 1/313 600/103 |
| 2015/0320436 | A1* | 11/2015 | Agee ................. A61B 1/00087 600/104 |
| 2020/0107850 | A1* | 4/2020 | Mirza .................... A61B 1/317 |
| 2021/0030513 | A1* | 2/2021 | Pajunk-Schelling .. A61B 17/32 |
| 2023/0240699 | A1 | 8/2023 | Intintoli et al. |
| 2024/0374278 | A1 | 11/2024 | Goldman |

OTHER PUBLICATIONS

Fernandes, Carlos Henrique et al. "Carpal tunnel release using the Paine retinaculotome inserted through a palmar incision", American Association for Hand Surgery, Oct. 16, 2023.
Office Action in U.S. Appl. No. 19/422,036 dated Apr. 10, 2026.

* cited by examiner

4/9

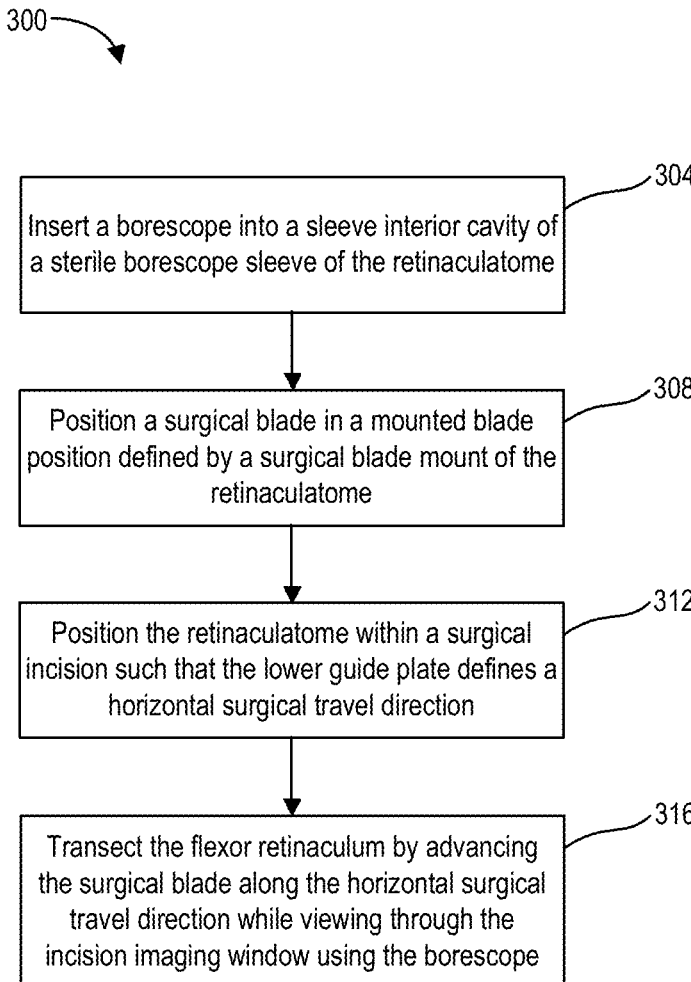

300

Insert a borescope into a sleeve interior cavity of a sterile borescope sleeve of the retinaculatome — 304

Position a surgical blade in a mounted blade position defined by a surgical blade mount of the retinaculatome — 308

Position the retinaculatome within a surgical incision such that the lower guide plate defines a horizontal surgical travel direction — 312

Transect the flexor retinaculum by advancing the surgical blade along the horizontal surgical travel direction while viewing through the incision imaging window using the borescope — 316

FIG. 3

RETINACULATOME AND A METHOD OF TRANSECTING A FLEXOR RETINACULUM IN A CARPAL TUNNEL RELEASE SURGERY USING THE RETINACULATOME

FIELD

This disclosure relates to a retinaculatome and a method of transecting a flexor retinaculum in a carpal tunnel release surgery using said retinaculatome.

Introduction

Carpal tunnel syndrome is a condition that can cause symptoms like numbness, tingling, pain, and/or weakness in the hand. Carpal tunnel syndrome occurs when the median nerve in the wrist is compressed. The median nerve passes through a passageway called the carpal tunnel in the wrist. The carpal tunnel is narrow and so any swelling can pinch the median nerve and cause symptoms like numbness, tingling, pain, and/or weakness in the hand.

Carpal tunnel release is surgery that can be performed to address carpal tunnel syndrome. In carpal tunnel release surgery, the flexor retinaculum (also known as the transverse carpal ligament) that forms the anterior roof of the carpal tunnel is transected to relieve the pressure on the median nerve.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In one aspect, a retinaculatome for cutting the flexor retinaculum in a carpal tunnel release surgery is disclosed. The retinaculatome includes a sterile borescope sleeve, a lower guide plate and a surgical blade mount. The sterile borescope sleeve includes a sleeve interior cavity and a sleeve exterior shell. The sleeve exterior shell extends between a sleeve distal end and a sleeve proximal end. The sleeve proximal end is dimensioned for removable borescope insertion. The sleeve exterior shell is sealed along its length and sealed at the sleeve distal end. The sleeve exterior shell is open or openable at the sleeve proximal end. The sleeve distal end has an incision imaging window transparent to the sleeve interior cavity. The lower guide plate extends from the sleeve distal end. The surgical blade mount is connected to the lower guide plate. The surgical blade mount defines a mounted blade position overlying the lower guide plate. The incision imaging window faces the mounted blade position.

In another aspect, a method of transecting a flexor retinaculum in a carpal tunnel release surgery using a retinaculatome is provided. The method includes inserting a borescope into a sleeve interior cavity of a sterile borescope sleeve of the retinaculatome. The sterile borescope sleeve includes a sleeve exterior shell that is sealed along its length and sealed at a sleeve distal end. The sleeve distal end has an incision imaging window transparent to the sleeve interior cavity. The method further includes positioning a surgical blade in a mounted blade position defined by a surgical blade mount connected to a lower guide plate extending from the sleeve distal end. The mounted blade position overlies the lower guide plate. The method further includes positioning the retinaculatome within a surgical incision such that the lower guide plate defines a horizontal surgical travel direction; and transecting the flexor retinaculum by advancing the surgical blade along the horizontal surgical travel direction while viewing through the incision imaging window using the borescope.

It will be appreciated by a person skilled in the art that an apparatus or method disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which:

FIG. 3 is a flowchart of an example method of transecting a flexor retinaculum in a carpal tunnel release surgery using the retinaculatome of FIGS. 1A-1C.

Figure 1A:
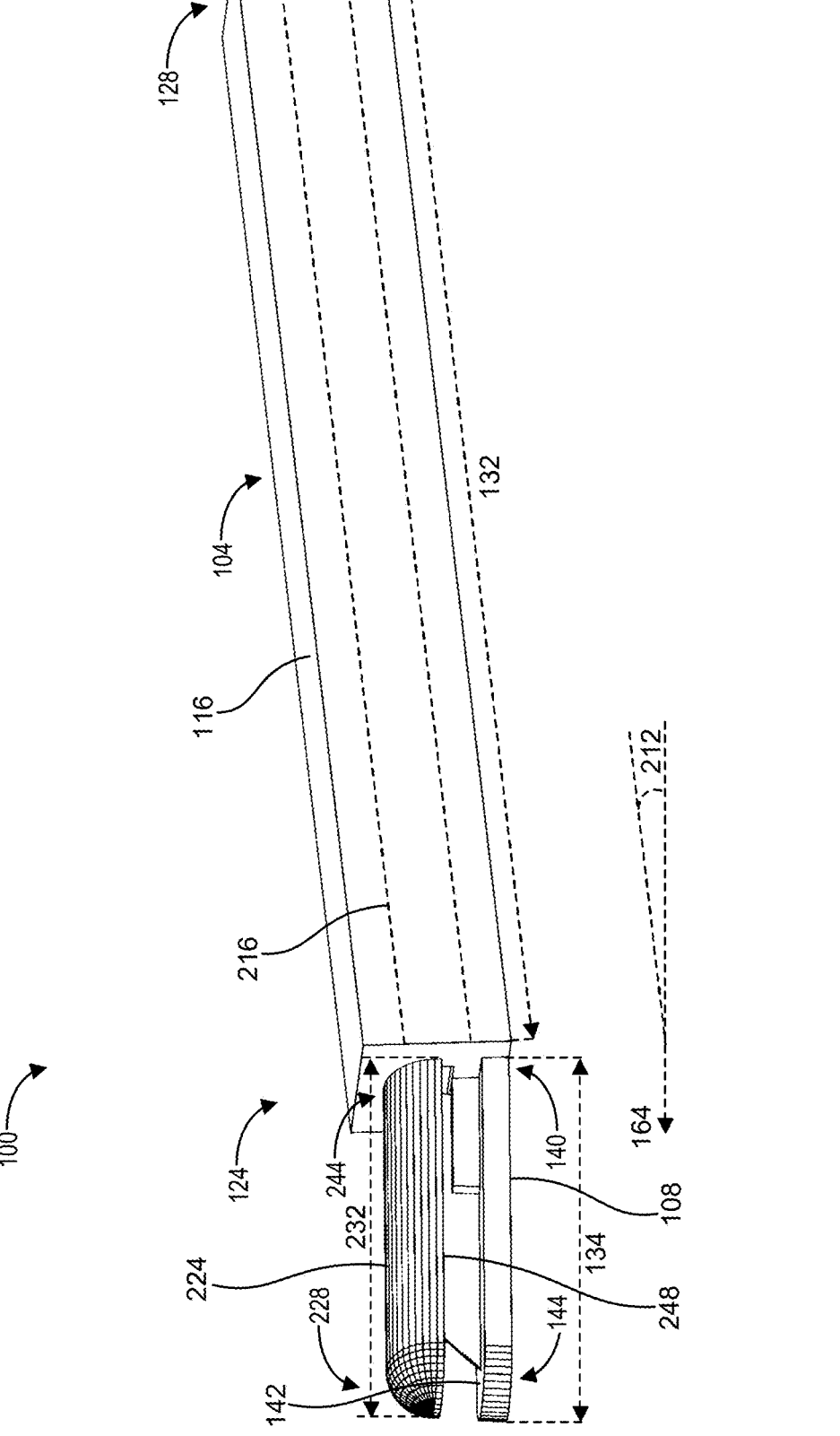
FIG. 1A is a side perspective view of a retinaculatome, in accordance with an embodiment.

The drawings included herewith are for illustrating various examples of apparatuses, methods, and instruments of the teaching of the present specification and are not intended to limit the scope of what is taught in any way.

DESCRIPTION OF EXAMPLE EMBODIMENTS

Various apparatuses, methods and instruments are described below to provide an example of an embodiment of each claimed invention. No embodiment described below limits any claimed invention and any claimed invention may cover apparatuses, methods, and instruments that differ from those described below. The claimed inventions are not limited to apparatuses, methods and instruments having all of the features of any one apparatus, method or instrument described below or to features common to multiple or all of the apparatuses, methods or instruments described below. It is possible that an apparatus, method or instrument described below is not an embodiment of any claimed invention. Any invention disclosed in an apparatus, method or instrument described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

The terms "an embodiment", "embodiment", "embodiments", "the embodiment", "the embodiments", "one or more embodiments", "some embodiments", and "one embodiment" mean "one or more (but not all) embodiments of the present invention(s)", unless expressly specified otherwise.

The terms "including", "comprising", and variations thereof mean "including but not limited to", unless expressly specified otherwise. A listing of items does not imply that any or all of the items are mutually exclusive, unless expressly specified otherwise. The terms "a", "an", and "the" mean "one or more", unless expressly specified otherwise.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used herein and in the claims, two or more parts are said to be "coupled", "connected", "attached", "joined", "affixed", or "fastened" where the parts are joined or operate together either directly or indirectly (i.e., through one or more intermediate parts), so long as a link occurs. As used herein and in the claims, two or more parts are said to be "directly coupled", "directly connected", "directly attached", "directly joined", "directly affixed", or "directly fastened" where the parts are connected in physical contact with each other. As used herein, two or more parts are said to be "rigidly coupled", "rigidly connected", "rigidly attached", "rigidly joined", "rigidly affixed", or "rigidly fastened" where the parts are coupled so as to move as one while maintaining a constant orientation relative to each other. None of the terms "coupled", "connected", "attached", "joined", "affixed", and "fastened" distinguish the manner in which two or more parts are joined together.

Further, although method steps may be described (in the disclosure and/or in the claims) in a sequential order, such methods may be configured to work in alternate orders. In other words, any sequence or order of steps that may be described does not necessarily indicate a requirement that the steps be performed in that order. The steps of methods described herein may be performed in any order that is practical. Further, some steps may be performed simultaneously.

As used herein and in the claims, a first element is said to be "communicatively coupled to" or "communicatively connected to" or "connected in communication with" a second element where the first element is configured to send or receive electronic signals (e.g., data) to or from the second element, and the second element is configured to receive or send the electronic signals from or to the first element. The communication may be wired (e.g., the first and second elements are connected by one or more data cables), or wireless (e.g., at least one of the first and second elements has a wireless transmitter, and at least the other of the first and second elements has a wireless receiver). The electronic signals may be analog or digital. The communication may be one-way or two-way. In some cases, the communication may conform to one or more standard protocols (e.g., SPI, $I^2C$, Bluetooth™, or IEEE™ 802.11).

As used herein and in the claims, a group of elements are said to "collectively" perform an act where that act is performed by any one of the elements in the group, or performed cooperatively by two or more (or all) elements in the group.

Some elements herein may be identified by a part number, which is composed of a base number followed by an alphabetical or subscript-numerical suffix (e.g., $112a$, or $112_1$). Multiple elements herein may be identified by part numbers that share a base number in common and that differ by their suffixes (e.g., $112_1$, $112_2$, and $112_3$). All elements with a common base number may be referred to collectively or generically using the base number without a suffix (e.g., 112).

The disclosed retinaculatome and the disclosed method of transecting a flexor retinaculum using the retinaculatome can be used during carpal tunnel release surgery. The disclosed retinaculatome and method can enable a minimally invasive surgical technique wherein the retinaculatome is inserted into a patient through a small incision.

The disclosed retinaculatome has a sterile borescope sleeve that includes a sleeve exterior shell and a sleeve interior cavity. The disclosed retinaculatome enables a non-sterile borescope to be positioned with the sleeve interior cavity during carpal tunnel release surgery. This can enable usage of a non-sterile borescope during the surgery. The sterile borescope sleeve can be disposed after the surgery while the borescope can be reused. The disclosed retinaculatome and method can mitigate the technical complexities and cost associated with requiring a sterile endoscope for minimally invasive carpal tunnel release surgery.

The disclosed retinaculatome may include an incision imaging window that can be at or above a mounted blade position to enable imaging using the borescope positioned within the sleeve interior cavity. This can provide improved visibility of the anatomical area being operated on compared with an incision imaging window that is below the mounted blade position.

In some embodiments, the disclosed retinaculatome includes a tissue shield. The tissue shield can mitigate visibility issues caused by falling tissue when the retinaculatome is advanced to transect the flexor retinaculum during surgery.

Figure 1B:
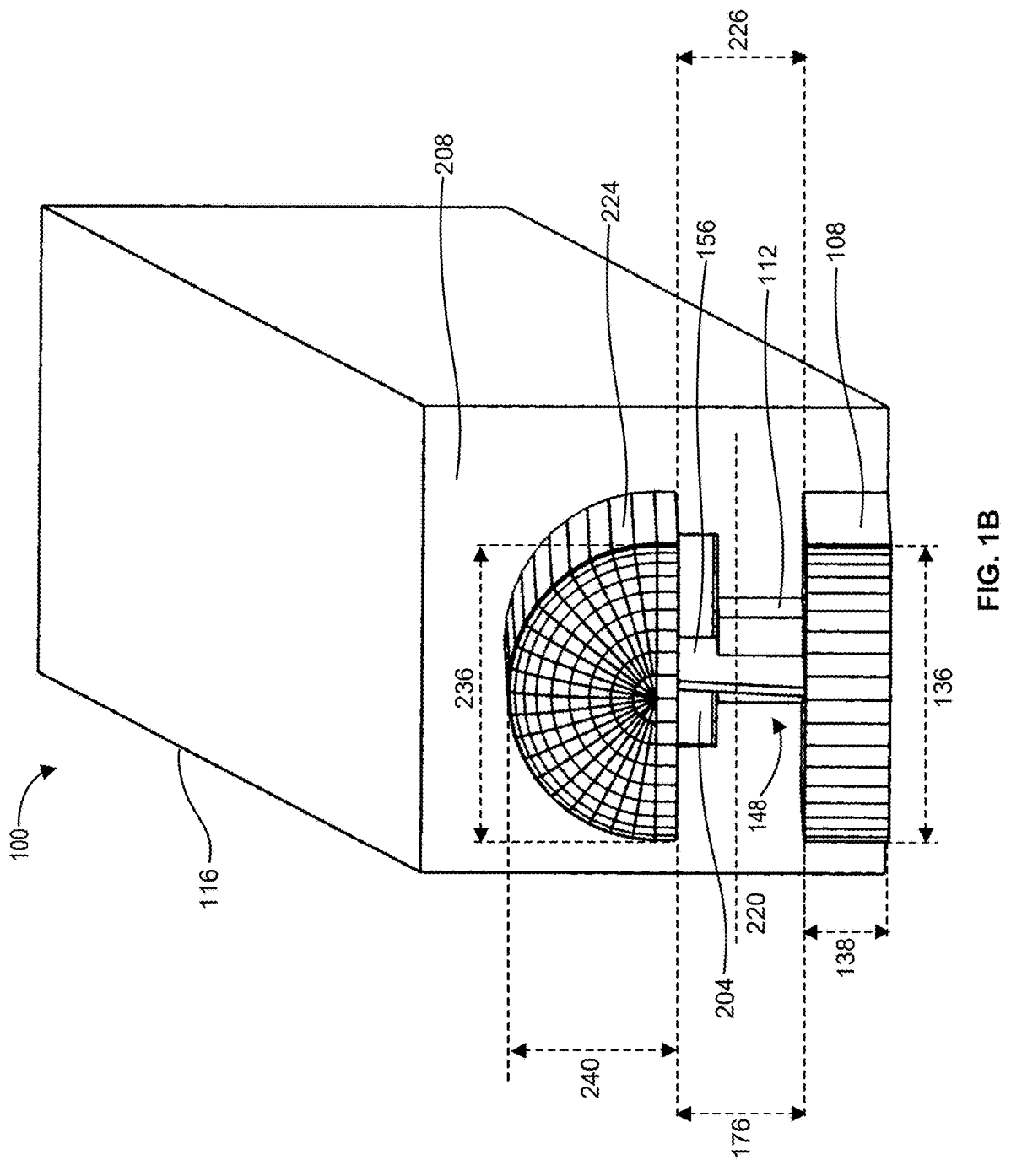
FIG. 1B is front perspective view of the retinaculatome of FIG. 1A.
Figure 1C:
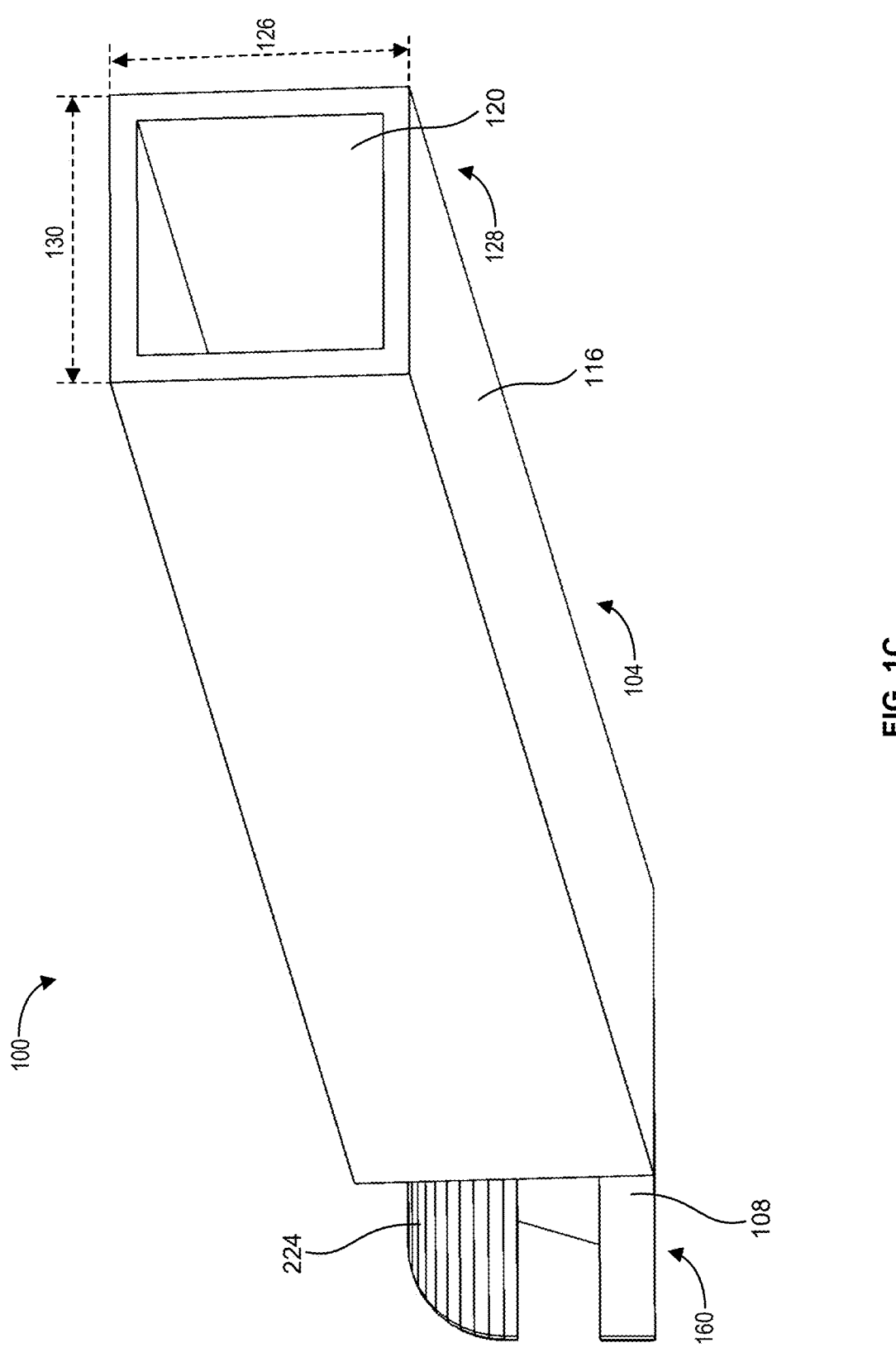
FIG. 1C is rear perspective view of the retinaculatome of FIG. 1A.

Reference is first made to FIGS. 1A-1C. FIG. 1A is a side perspective view of a retinaculatome 100. FIG. 1B is a front perspective view of retinaculatome 100. FIG. 1C is a rear perspective view of retinaculatome 100. In the illustrated embodiment, retinaculatome 100 includes a sterile borescope sleeve 104, a lower guide plate 108 and a surgical blade mount 112.

Borescope sleeve 104 may include a sleeve exterior shell 116 and a sleeve interior cavity 120. Sleeve exterior shell 116 may have any suitable cross-sectional shape that defines sleeve interior cavity 120. For example, sleeve exterior shell 116 may have a square, a rectangular, a circular, an oval, or an irregular cross-sectional shape.

Sleeve exterior shell 116 may extend between a sleeve distal end 124 and a sleeve proximal end 128. Sleeve exterior shell 116 may have a sleeve length 132 between sleeve distal end 124 and sleeve proximal end 128. Sleeve exterior shell 116 may have any sleeve length 132 that is suitable for use during carpal tunnel release surgery and is sufficient to accommodate a suitable imaging device (e.g., a borescope) within sleeve interior cavity 120. In some embodiments, sleeve length 132 may be at least 7 cm. For example, sleeve length 132 may be 7-15 cm. In other embodiments, a more compact design may be utilized and sleeve length 132 may be smaller than 7 cm (e.g., 3-6.9 cm).

Sleeve exterior shell 116 may be sealed along sleeve length 132 and at sleeve distal end 124. This can enable an unsterilized imaging device (e.g., a borescope) to be safely positioned within sleeve interior cavity 120 during a surgical procedure. The borescope may have a built-in light source. In some embodiments, a separate light source may be positioned within sleeve interior cavity 120.

In some embodiments, sleeve exterior shell 116 may be open or openable at sleeve proximal end 128. The open or openable sleeve proximal end 128 may be dimensioned for removable insertion of a borescope into sleeve interior cavity 120. For an example embodiment where sleeve exterior shell 116 has a rectangular cross-section, at sleeve proximal end 128, sleeve exterior shell 116 may have a sleeve width 130 of 2-20 mm and a sleeve height 126 of 2-20 mm. In some embodiments, sleeve exterior shell 116 may have a rectangular cross-section with a different sleeve width 130 and/or sleeve height 126. In other embodiments, sleeve exterior shell 116 may have a non-rectangular cross-section (e.g. another regular cross-section—such as circular or hexagonal, or an irregular cross-section).

The imaging device of the borescope may have any focal length that is suitable for use with retinaculatome 100 in a carpal tunnel release surgery. In some embodiments, the focal length may be 1-10 cm. In other embodiments, the focal length may be different.

In some embodiments, sleeve exterior shell 116 may be open at sleeve proximal end 128. A borescope may be inserted into sleeve interior cavity 120 for a surgical procedure. Sleeve exterior shell 116 may remain open at sleeve proximal end 128 during the surgical procedure. The surgical procedure may be performed while preventing the open sleeve proximal end 128 (and the borescope positioned within sleeve interior cavity 120) from coming into direct contact with the patient.

Figure 1D:
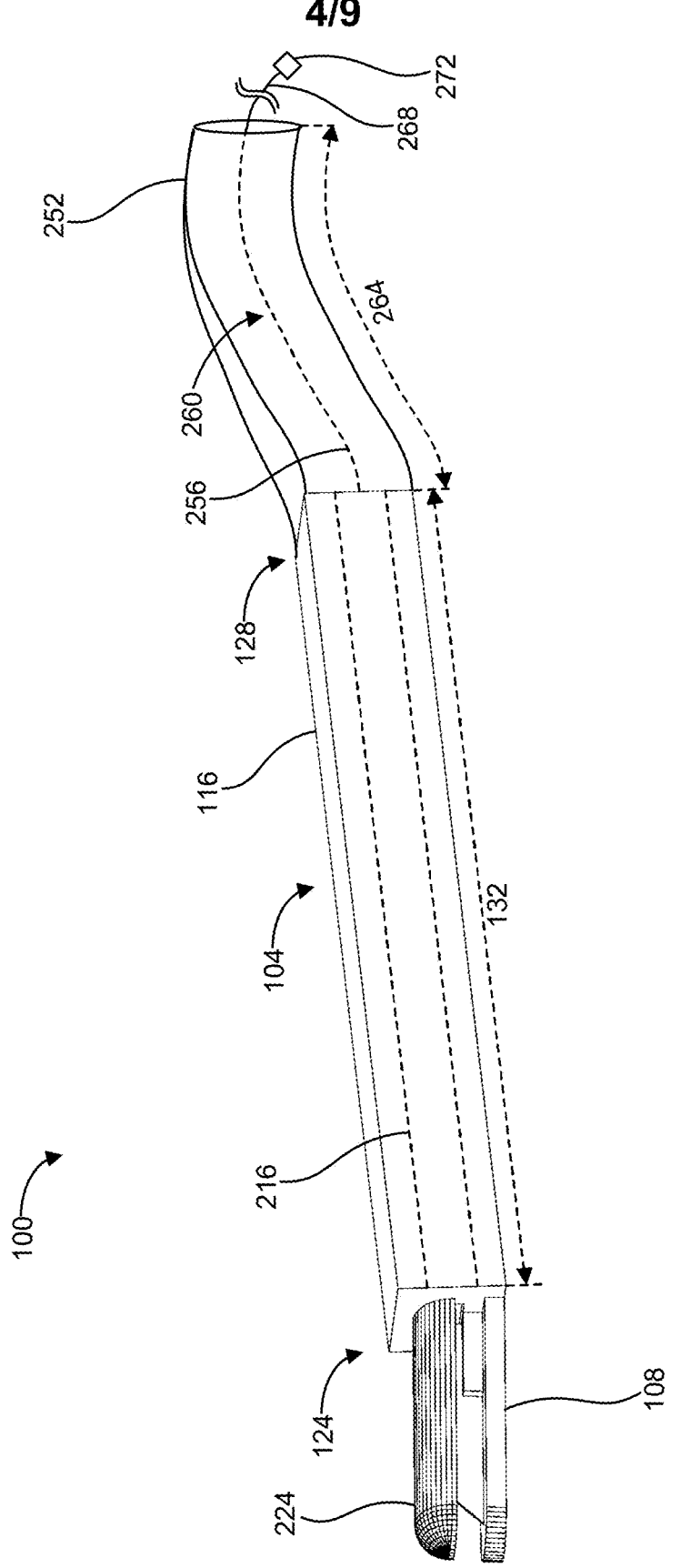
FIG. 1D is a side perspective view of the retinaculatome of FIG. 1A with an extension sheath connected to the retinaculatome, in accordance with an embodiment.

In some embodiments, retinaculatome 100 may include an extension sheath connected to sterile borescope sleeve 104. Reference is now additionally made to FIG. 1D, which is a side perspective view of retinaculatome 100 with an extension sheath 252 connected to sleeve exterior shell 116 at sleeve proximal end 128.

In the illustrated example embodiment, borescope 216 positioned within sleeve interior cavity 120 includes a non-sterile borescope cable 256 (e.g., a data communication cable) that extends out of sleeve interior cavity 120 at sleeve proximal end 128. Extension sheath 252 can provide a sterile covering for a distal cable portion 260 of non-sterile borescope cable 256 that is within an operative sterile field during use of retinaculatome 100. A proximal cable portion 268 of non-sterile borescope cable 256 that is outside of the operative sterile field may be exposed out of extension sheath 252. Proximal cable portion 268 may include an electrical connector 272. Electrical connector 272 may include, for example, a data connector to transfer borescope data to an external device.

Extension sheath 252 may be made using any suitable materials that are sterile when formed or compatible with sterilization. For example, extension sheath 252 may be made using a sterile plastic material. Preferably, extension sheath 252 may be made using a flexible material to enable borescope cable 256 to flex during use of retinaculatome

100. Extension sheath 252 may have any suitable cross-sectional shape and size to enclose distal cable portion 260 within extension sheath 252. Extension sheath 252 may have any suitable sheath length 264 to cover distal cable portion 260 that can be within an operative sterile field during use. For example, sheath length 264 may be 0.3-6 m.

In some embodiments, sleeve exterior shell 116 may be closed at proximal end 128 during a surgical procedure but may be openable before and after the surgical procedure. Before the surgical procedure, sleeve exterior shell 116 may be opened at proximal end 128 to insert a borescope (e.g., a wireless borescope) into sleeve interior cavity 120. Sleeve exterior shell 116 may then be closed at proximal end 128 to fully enclose the borescope within sleeve exterior shell 116 during the surgical procedure. After the surgical procedure is completed, sleeve exterior shell 116 may be opened to remove the borescope from sleeve interior cavity 120.

In some embodiments, sleeve proximal end 128 may not be open or openable. For example, a wireless borescope may be sealed within sleeve exterior shell 116 and not be removable. The borescope may be disposed along with borescope sleeve 104 after each use.

Sleeve exterior shell 116 may be made using any suitable material that can be manufactured into a biocompatible, sterile state or that is compatible with sterilization (e.g. by chemical means or heat) after it is formed in the manufacturing process. For example, sleeve exterior shell 116 may be made using plastic, metal and/or glass materials that are sterile when formed or compatible with sterilization. Preferably, sleeve exterior shell 116 is formed of a rigid material that will not collapse when grasped by hand and manually advanced through an incision to perform the surgery.

Lower guide plate 108 may extend from sleeve distal end 124. Lower guide plate can act as a guidance structure that helps guide (i.e. direct) retinaculatome 100 along an intended anatomical path and minimizes deviation from the intended anatomical path during a surgical procedure. In some embodiments, lower guide plate 108 can act as a stabilizing platform and provide a consistent under-surface against which a tissue can be cut by a surgical blade mounted on retinaculatome 100.

Lower guide plate 108 may have any suitable shape and dimensions that can provide the guidance and/or stabilizing platform functionality to retinaculatome 100. In the illustrated example embodiment, a lower guide plate distal end 144 of lower guide plate 108 is arcuate. This may reduce resistance and/or improve guidance when retinaculatome 100 is advanced through tissue during a surgical procedure. In some embodiments, lower guide plate distal end 144 may not be arcuate. For example, lower guide plate distal end 144 can be straight. This may reduce manufacturing complexity of retinaculatome 100.

In the illustrated example embodiment, lower guide plate 108 has a rectangular plate structure between lower guide plate distal end 144 and a lower guide plate proximal end 140. Lower guide plate 108 may have a substantially constant lower guide plate width 136 between lower guide plate proximal end 140 and lower guide plate distal end 144. A substantially constant lower guide plate width 136 can reduce manufacturing complexity. In some embodiments, lower guide plate width 136 may decrease gradually between lower guide plate proximal end 140 and lower guide plate distal end 144. This may reduce resistance and/or improve guidance when retinaculatome 100 is advanced through tissue during a surgical procedure.

Lower guide plate width 136 may be same or different compared with sleeve width 130 of sleeve exterior shell 116.

In some embodiments, lower guide plate 108 may have a total lower guide plate length 134 of 1-6 cm, lower guide plate width 136 of 2-10 mm, and a lower guide plate thickness 138 of 1-3 mm. In other embodiments, lower guide plate 108 may have a different lower guide plate length 134, lower guide plate width 136 and/or lower guide plate thickness 138.

Lower guide plate 108 may be made using any suitable material that can be manufactured into a biocompatible, sterile state or that is compatible with sterilization (e.g. by chemical means or heat) after it is formed in the manufacturing process. For example, lower guide plate 108 may be made using plastic, metal and/or glass materials that are sterile when formed or compatible with sterilization.

Surgical blade mount 112 may be connected to lower guide plate 108. Surgical blade mount 112 can define a mounted blade position 148 overlying lower guide plate 108. Surgical blade mount 112 may have any design suitable for mounting of a surgical blade 156 in mounted blade position 148. In some embodiments, surgical blade mount 112 may have a side slotted fitting capable of receiving a standard surgical blade. In other embodiments, surgical blade mount 112 may have a different design (e.g. a mounting connection suitable for a non-standard surgical blade). This may permit surgical blade mount 112 to secure a surgical blade that is specially sized and shaped for carpal tunnel surgery.

Surgical blade 156 may have any size suitable for use during a carpal tunnel release surgery. For example, surgical blade 156 may have a surgical blade height 176 of 3-10 mm. In some embodiments, lower guide plate 108 includes a void designed to accommodate a standard surgical blade 156 mounted in mounted blade position 148. In other embodiments, the relative sizes and positions of the components may be selected so that surgical blade 156 can be accommodated in mounted blade position 148 without needing a void in lower guide plate 108.

During a carpal tunnel release surgery, retinaculatome 100 may generally be advanced along a horizontal surgical travel direction 164 to transect a flexor retinaculum using surgical blade 156 that is mounted in mounted blade position 148. Horizontal surgical travel direction 164 may be defined with reference to retinaculatome 100. In the illustrated example, horizontal surgical travel direction 164 is defined as a direction substantially parallel to lower guide plate 108. Retinaculatome 100 may be utilized in any suitable orientation during a surgical procedure. Based on the orientation of retinaculatome 100 itself, horizontal surgical travel direction 164 may or may not be horizontal with reference to the local surface of the Earth.

In some embodiments, lower guide plate 108 may be designed to match a type of surgical blade that is used with retinaculatome 100. In the illustrated example embodiment, surgical blade 156 has a fixed and straight cutting edge 168 that is at an oblique angle 172 to lower guide plate 108. Along horizontal surgical travel direction 164, lower guide plate distal end 144 extends beyond a surgical blade distal end 160 of surgical blade 156. This can enable lower guide plate 108 to provide underlying support to the flexor retinaculum when it is transected by surgical blade 156. As an example, lower guide plate distal end 144 may extend beyond surgical blade distal end 160 by 1-20 mm. In other embodiments, lower guide plate 108 and/or surgical blade 156 may be differently designed. For example, lower guide plate distal end 144 may not extend beyond surgical blade distal end 160. Surgical blade 156 and lower guide plate 108 may extend to substantially the same position along horizontal surgical travel direction 164.

Reference is now additionally made to FIGS. 2A-2I, which are schematic cross-sectional views of surgical blades 156a-156i connected to lower guide plate 108, in accordance with various example embodiments.

Figure 2A:
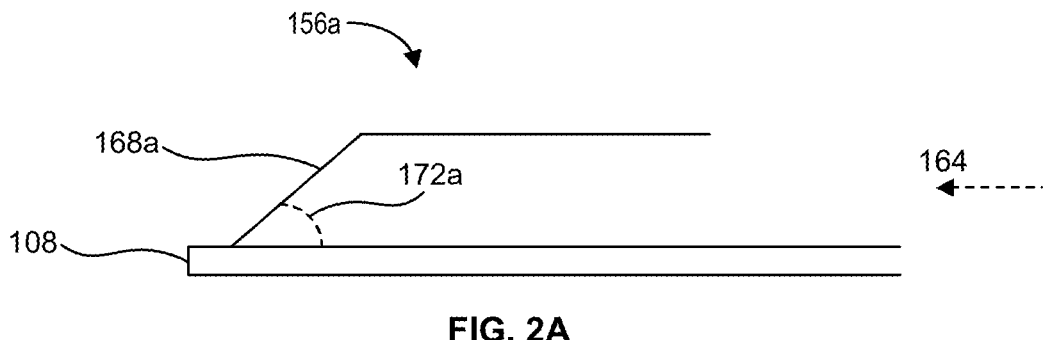
FIGS. 2A-2I are schematic cross-sectional views of example surgical blades mounted on the retinaculatome of FIGS. 1A-1C.
Figure 2B:
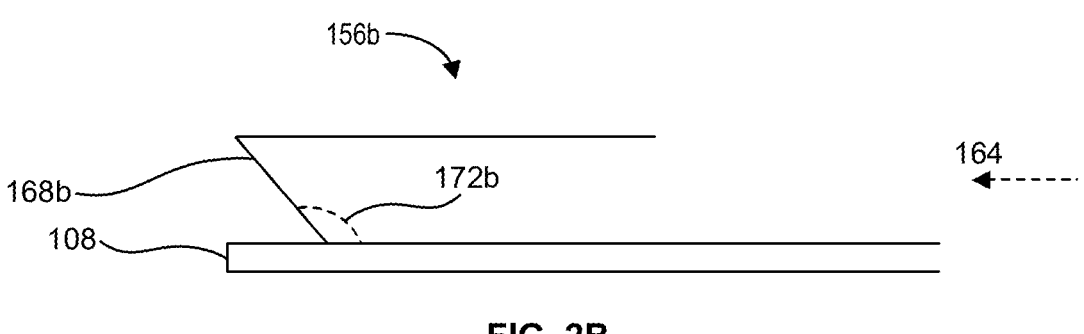

FIGS. 2A and 2B show surgical blades 156a and 156b respectively that have a fixed and straight cutting edge 168 that is at an oblique angle 172 to lower guide plate 108. Cutting edge 168 may slope downwards distally along horizontal surgical travel direction 164 (e.g., cutting edge 168a) or may slope upwards distally along horizontal surgical travel direction 164 (e.g., cutting edge 168b).

Figure 2C:
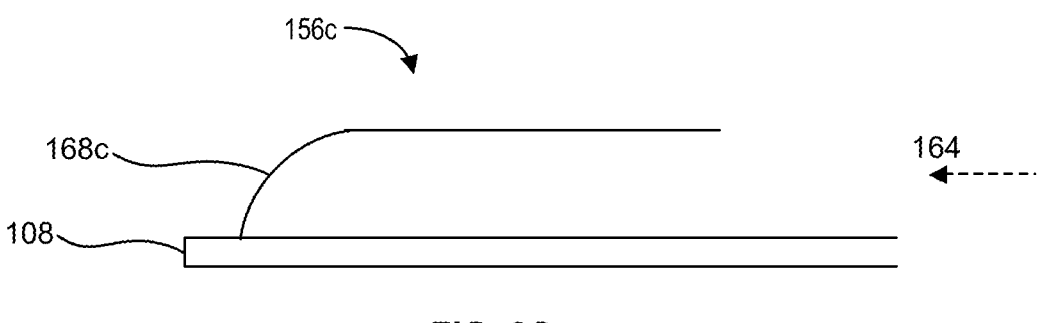
Figure 2D:
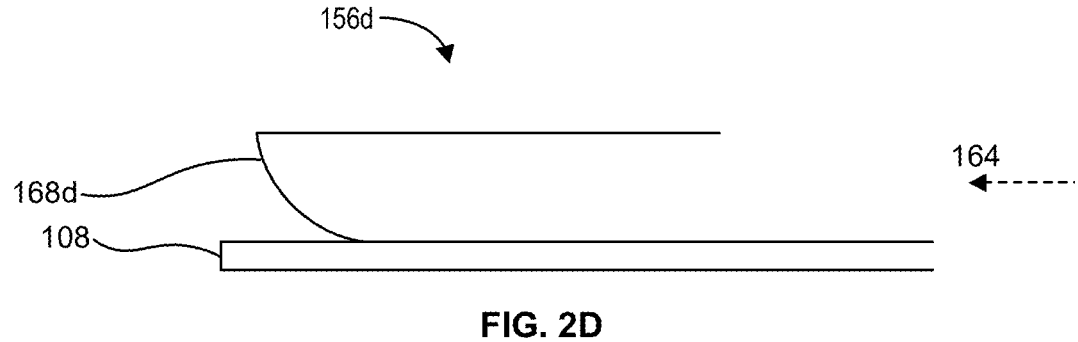

FIGS. 2C and 2D show surgical blades 156c and 156d respectively that have a fixed and curved cutting edge 168. Cutting edge 168 may curve downwards distally along horizontal surgical travel direction 164 (e.g., cutting edge 168c) or may curve upwards distally along horizontal surgical travel direction 164 (e.g., cutting edge 168d).

Figure 2E:
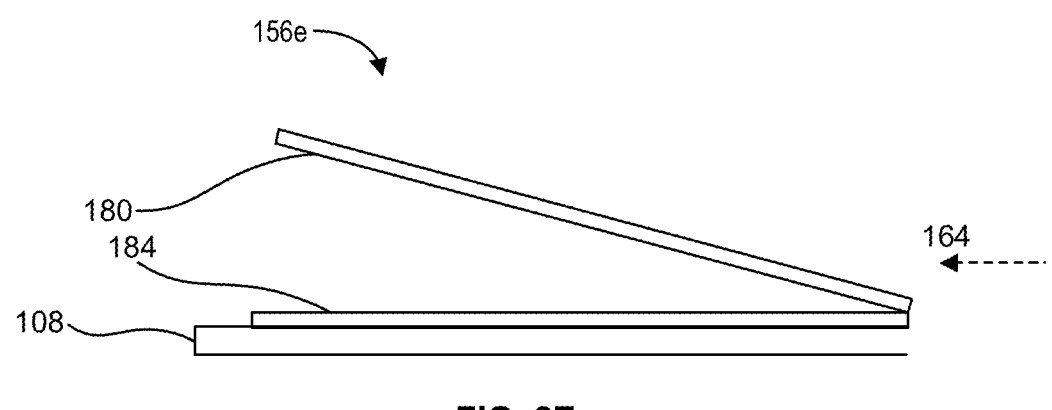

FIG. 2E shows surgical blade 156e that has two opposing blade surfaces 180 and 184. At least one of the two blade surfaces 180 and 184 may be movable to provide a scissor-type cutting action. In some embodiments, the movable blade surface may be connected to a motor. The scissor-type cutting action may be controllable using a switch/button by a medical practitioner.

Figure 2F:
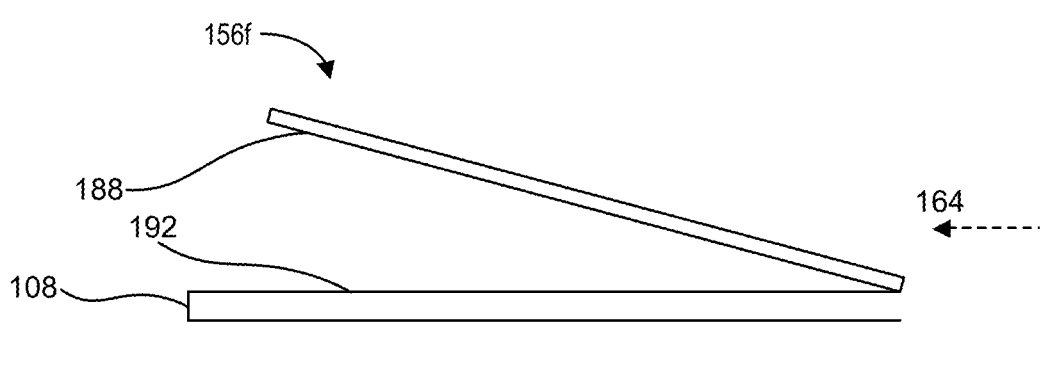

FIG. 2F shows surgical blade 156f that has a movable sharp blade surface 188 that provides a cutting action in combination with another surface 192. In FIG. 2F, the other surface 192 includes a fixed edge of lower guide plate 108. Blade surface 188 may be moved to provide a paper-cutter type cutting action along fixed edge 192. In some embodiments, the other surface 192 may be provided by a groove formed on an upper surface of lower guide plate 108. The movable sharp blade surface 188 may be connected to a motor. The cutting action provided by blade surface 188 may be controllable using a switch/button by a medical practitioner.

Figure 2G:
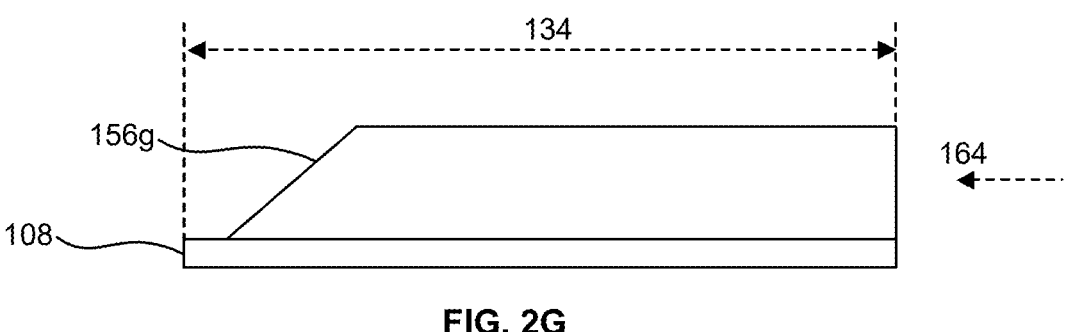
Figure 2H:
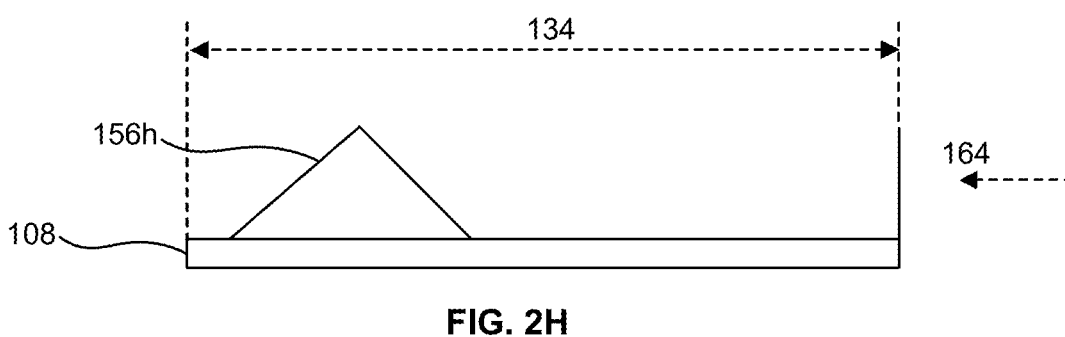
Figure 2I:
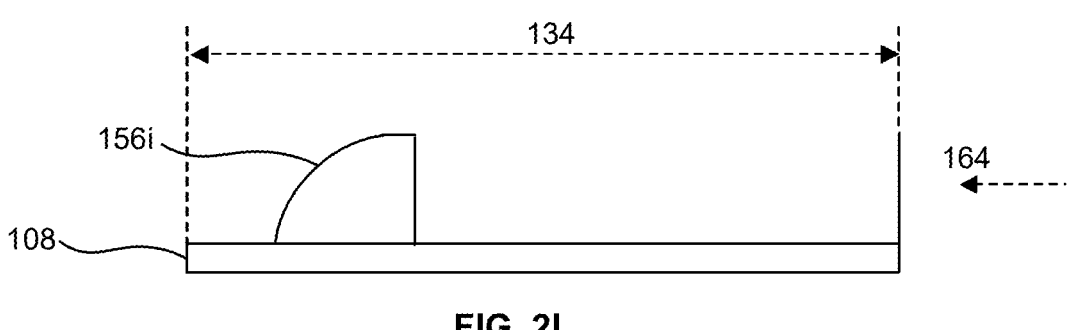

In some embodiments, surgical blade 156, when mounted in mounted blade position 148, may extend along a substantially entire portion of lower guide plate length 134. For example, FIG. 2G shows surgical blade 156g that extends along a substantially entire portion of lower guide plate length 134. In some embodiments, surgical blade 156, when mounted in the mounted blade position, may extend along a small portion (e.g., less than 50%) of lower guide plate length 134. For example, FIG. 2H and FIG. 2I show surgical blades 156h and 156i respectively that extend along a small portion of lower guide plate length 134.

Returning to FIGS. 1A-1C, sleeve distal end 124 may have an incision imaging window 204 that is transparent to sleeve interior cavity 120. Incision imaging window 204 may face mounted blade position 148.

Incision imaging window 204 may have any suitable position, shape and size to enable an imaging device positioned within sleeve interior cavity 120 to image an anatomical area that surgical blade 156 is being used in. In the illustrated example embodiment, incision imaging window 204 is defined as a circular shaped window on a distal end surface 208 of sleeve exterior shell 116. A portion of incision imaging window 204 may be at least at or above a middle 220 of mounted blade position 148. Sleeve exterior shell 116 may have an inclination of 0-45° (preferably, 5-10°) relative to horizontal surgical travel direction 164. Incision imaging window 204, that is defined on distal end surface 208 of sleeve exterior shell 116, can therefore provide a viewing inclination 212 of 0-45° (preferably, 5-10°) relative to horizontal surgical travel direction 164. Incision imaging window 204 can enable an imaging device (e.g., a camera of a borescope 216) positioned within sleeve interior cavity 120 to have a vertical position that is at least at or above a middle 220 of mounted blade position 148 and a downward viewing angle of 0-45° (preferably, 5-10°). The vertical positioning of incision imaging window 204 with respect to mounted blade position 148 and the viewing inclination angle (preferably, 5-10°) may provide improved imaging of the anatomical area as surgical blade 156 is advanced during a surgical procedure. The viewing angle may be designed based at least in part on a type of borescope intended for use with retinaculatome 100. For example, sleeve exterior shell 116 may have a shorter sleeve length 132 (e.g., 3-7 cm) and a smaller inclination of 0-2° relative to horizontal surgical travel direction 164 when designed for use with shorter borescopes. In such applications, a smaller viewing angle (0-2°) may provide sufficient imaging performance using the shorter borescope.

In some embodiments, incision imaging window 204 may have a different position, shape and/or size. For example, incision imaging window 204 may be formed as a square or rectangular shaped window. As another example, entire distal end surface 208 may be made using a transparent material. The entire distal end surface 208 may define incision imaging window 204. This may enable a larger area to be imaged during the surgical procedure.

Incision imaging window 204 may be made using any suitable material that can be manufactured into a biocompatible, sterile state or that is compatible with sterilization (e.g. by chemical means or heat) after it is formed in the manufacturing process, and that is sufficiently transparent to enable imaging using an imaging device positioned within sleeve interior cavity 120. For example, incision imaging window 204 may be made using plastic and/or glass materials that are sterile when formed or compatible with sterilization and are substantially transparent (i.e. at least 75% transparency to visible light, preferably at least 95% transparency to visible light).

In some embodiments, incision imaging window 204 may be integrally formed with sleeve exterior shell 116. Incision imaging window 204 and sleeve exterior shell 116 may both be formed using the same material that is compatible with sterilization and is substantially transparent. In some embodiments, incision imaging window 204 and sleeve exterior shell 116 may be formed using different materials.

In some embodiments, retinaculatome 100 includes a tissue shield 224 that extends from sleeve distal end 124. Tissue shield 224 may be vertically spaced above lower guide plate 108 by a shield spacing 226. Shield spacing 226 may be defined as the smallest distance between an upper surface 142 of lower guide plate 108 and a lower edge 248 of tissue shield 224. Tissue shield 224 can shield mounted blade position 148. During a surgical procedure, surgical blade 156 can cut through tissue when retinaculatome 100 is advanced along horizontal surgical travel direction 164. As retinaculatome 100 advances, surrounding tissue may fall over and obstruct imaging of the advancing surgical blade 156. Tissue shield 224 can mitigate this problem and improve visibility during the surgical procedure.

In other embodiments, retinaculatome 100 may not include a tissue shield 224. Other techniques may be utilized to address the above-noted problem. For example, a medical practitioner may utilize a separate instrument (e.g., a retractor) in addition to a retinaculatome without a tissue shield. However, this may require two-handed operation for the two separate instruments compared with a single-handed operation that can be enabled by a retinaculatome having a tissue shield.

Tissue shield 224 may have any suitable shape and dimensions that can provide the tissue shielding functionality to retinaculatome 100. In some embodiments, tissue shield 224 may have shield spacing 226 of 1-15 mm, a tissue shield length 232 of 2-8 cm, a tissue shield width 236 of 2-10 mm, and a tissue shield height 240 of 2-10 mm. In other embodiments, tissue shield 224 may have a different shield spacing 226, tissue shield length 232, tissue shield width 236, and/or tissue shield height 240.

Tissue shield length 232 may be the same or different compared with lower guide plate length 134. Tissue shield width 236 may be the same or different compared with lower guide plate width 136. Tissue shield height 240 may be the same or different compared with lower guide plate thickness 138.

In some embodiments, tissue shield 224 may have a substantially constant tissue shield width 236 between a tissue shield proximal end 244 and a tissue shield distal end 228. A substantially constant tissue shield width 236 may reduce manufacturing complexity. In some embodiments, tissue shield width 236 may decrease gradually from tissue shield proximal end 244 towards tissue shield distal end 228. This may reduce resistance when retinaculatome 100 is advanced through tissue during a surgical procedure.

In the illustrated example embodiment, tissue shield 224 is dome-shaped. In other embodiments, tissue shield 224 may be differently shaped. For example, tissue shield 224 may be formed using a combination of inclined or faceted surfaces.

In some embodiments, a tissue shield distal end 228 of tissue shield 224 may be arcuate. This may reduce resistance when retinaculatome 100 is advanced through tissue during a surgical procedure. In other embodiments, tissue shield distal end 228 may not be arcuate. This may reduce manufacturing complexity of retinaculatome 100.

Tissue shield 224 may be made using any suitable material that can be manufactured into a biocompatible, sterile state or that is compatible with sterilization (e.g. by chemical means or heat) after it is formed in the manufacturing process. For example, tissue shield 224 may be made using plastic, metal and/or glass materials that are sterile when formed or compatible with sterilization.

Figure 4:
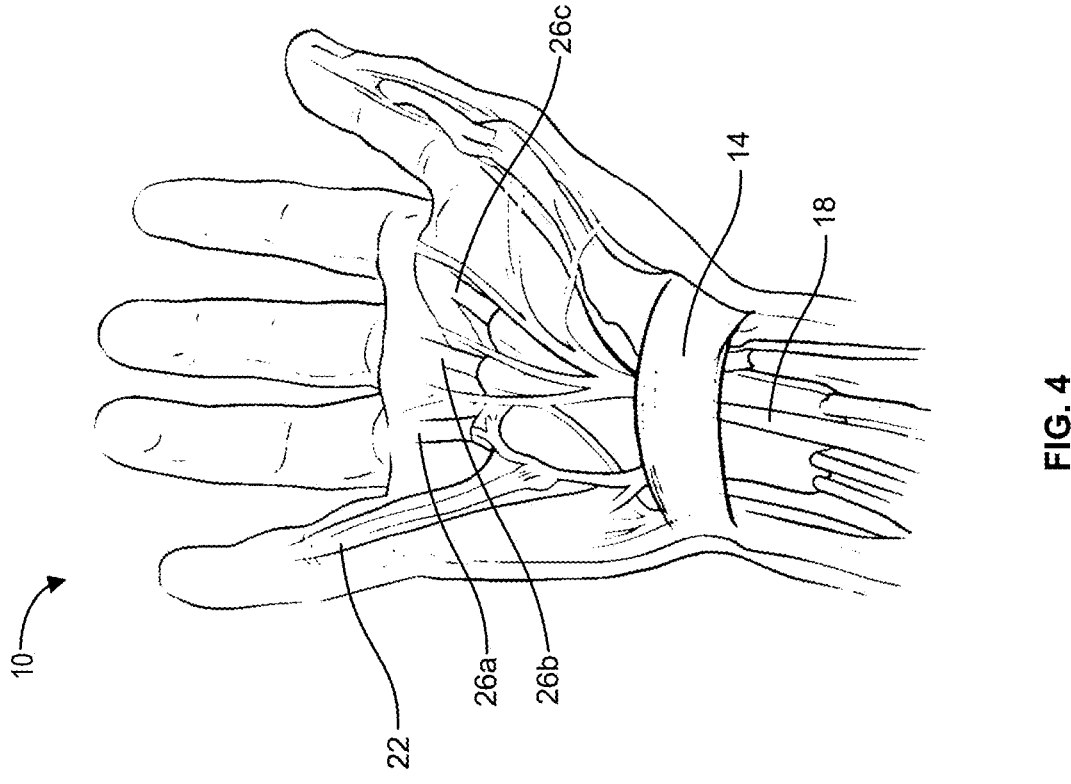
FIG. 4 is an anatomical diagram of a hand including a flexor retinaculum that can be transected using the example method of FIG. 3.

Reference is now made to FIGS. 3 and 4. FIG. 3 is a flowchart of a method 300 of transecting a flexor retinaculum in a carpal tunnel release surgery using a retinaculatome. FIG. 4 is an anatomical diagram of a hand 10 including a flexor retinaculum 14, a median nerve 18, a synovium 22 and flexor tendons 26. Method 300 may be implemented, for example, by retinaculatome 100 of FIGS. 1A-1C and concurrent reference is now made to components shown in FIGS. 1A-1C.

At 304, method 300 includes inserting a borescope into a sleeve interior cavity of a sterile borescope sleeve of the retinaculatome. For example, borescope 216 may be inserted into sleeve interior cavity 120 of sterile borescope sleeve 104.

Sleeve exterior shell 116 of sterile borescope sleeve 104 may be sealed along its length and sealed at sleeve distal end 124. This can enable a non-sterile borescope to be used with method 300. Sleeve proximal end 128 may be open to enable a borescope cable to extend out of sleeve interior cavity 120.

In some embodiments, a wireless borescope may be used. Sleeve proximal end 128 may be closed after the wireless borescope is inserted into the sleeve interior cavity. In some embodiments, a sterile endoscope may be used, and at 304, the endoscope is inserted into the sleeve interior cavity of the retinaculatome.

Sleeve distal end 124 may include an incision imaging window 204 that is transparent to sleeve interior cavity 120. Borescope 216 may be positioned within sleeve interior cavity 120 to optionally have a downward viewing angle (e.g. 0 to 45 degrees downwards from horizontal) towards a surgical blade 156 that can be mounted on retinaculatome 100. In some embodiments, sleeve exterior shell 116 may be substantially transparent. This may enable a larger area to be imaged by borescope 216.

At 308, method 300 includes positioning a surgical blade in a mounted blade position defined by a surgical blade mount of the retinaculatome. For example, a standard surgical blade 156 may be positioned in mounted blade position 148 defined by surgical blade mount 112. Surgical blade mount 112 may be connected to lower guide plate 108 and extend from sleeve distal end 124. Mounted blade position 148 defined by surgical blade mount 112 can be overlying lower guide plate 108.

At 312, method 300 includes positioning the retinaculatome within a surgical incision such that the lower guide plate defines a horizontal surgical travel direction. For example, retinaculatome 100 may be positioned within a surgical incision such that lower guide plate 108 defines a horizontal surgical travel direction 164.

At 316, method 300 includes transecting the flexor retinaculum by advancing the surgical blade along the horizontal surgical travel direction while viewing through the incision imaging window using the borescope. For example, surgical blade 156 may be advanced along horizontal surgical travel direction 164 to transect flexor retinaculum 14 while viewing through incision imaging window 204 using borescope 216.

In some embodiments, retinaculatome 100 includes a tissue shield 224 extending from sleeve distal end 124 and vertically spaced above lower guide plate 108. Tissue shield 224 can shield the mounted blade position and improve visibility while surgical blade 156 is advanced along horizontal surgical travel direction 164 to transect flexor retinaculum 14.

Method 300 may be implemented using any suitable surgical blade. For example, the flexor retinaculum may be transected using a fixed and straight cutting edge of surgical blade 156a (FIG. 2A) or 156b (FIG. 2B). As another example, the flexor retinaculum may be transected using a fixed and curved cutting edge of surgical blade 156c (FIG. 2C) or 156d (FIG. 2D). As another example, the flexor retinaculum may be transected using a scissor-type cutting action of surgical blade 156e (FIG. 2E).

In some embodiments, sterile borescope sleeve 104 may be disposed after the carpal tunnel release surgery is completed. Borescope 216 may be retained for reuse. In some embodiments, borescope 216 may be disposed after the carpal tunnel release surgery is completed.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

Items

Item 1: A retinaculatome for cutting the flexor retinaculum in a carpal tunnel release surgery, the retinaculatome comprising:
    a sterile borescope sleeve comprising:
        a sleeve interior cavity, and
        a sleeve exterior shell extending between a sleeve distal end and a sleeve proximal end,
        the sleeve distal end having an incision imaging window transparent to the sleeve interior cavity;
    a lower guide plate extending from the sleeve distal end; and
    a surgical blade mount connected to the lower guide plate.

Item 2: The retinaculatome of any other item, wherein the sleeve proximal end is dimensioned for removable borescope insertion.

Item 3: The retinaculatome of any other item, wherein the sleeve exterior shell is sealed along its length and sealed at the sleeve distal end, and is open or openable at the sleeve proximal end.

Item 4: The retinaculatome of any other item, wherein the surgical blade mount defines a mounted blade position overlying the lower guide plate, and wherein the incision imaging window faces the mounted blade position.

Item 5: The retinaculatome of any other item, further comprising a tissue shield extending from the sleeve distal end and vertically spaced above the lower guide plate to shield the mounted blade position.

Item 6: The retinaculatome of any other item, wherein the incision imaging window is positioned to provide a viewing inclination of 0-45° relative to a horizontal surgical travel direction.

Item 7: The retinaculatome of any other item, wherein a distal end of the lower guide plate is arcuate.

Item 8: The retinaculatome of any other item, wherein a sleeve length between the sleeve proximal end and the sleeve distal end is at least 3 cm.

Item 9: The retinaculatome of any other item, wherein a lower guide plate width is substantially constant between a lower guide plate proximal end and a lower guide plate distal end.

Item 10: The retinaculatome of any other item, wherein a lower guide plate width decreases gradually between a lower guide plate proximal end and a lower guide plate distal end.

Item 11: The retinaculatome of any other item, wherein the tissue shield is dome-shaped.

Item 12: The retinaculatome of any other item, wherein a distal end of the tissue shield is arcuate.

Item 13: The retinaculatome of any other item, wherein a tissue shield width is substantially constant between a tissue shield proximal end and a tissue shield distal end.

Item 14: The retinaculatome of any other item, wherein a tissue shield width decreases gradually between a tissue shield proximal end and a tissue shield distal end.

Item 15: The retinaculatome of any other item, further comprising a surgical blade mounted in the surgical blade mount.

Item 16: The retinaculatome of any other item, wherein a lower guide plate distal end extends beyond a surgical blade distal end along a horizontal surgical travel direction.

Item 17: The retinaculatome of any other item, wherein the surgical blade and the lower guide plate extend to a substantially same position along a horizontal surgical travel direction.

Item 18: The retinaculatome of any other item, wherein a distal end of the surgical blade comprises a fixed and straight cutting edge that is at an oblique angle to the lower guide plate.

Item 19: The retinaculatome of any other item, wherein a distal end of the surgical blade has a fixed and curved cutting edge.

Item 20: The retinaculatome of any other item, wherein the surgical blade comprises two opposing blade surfaces and at least one of the two opposing blade surfaces is movable to provide a scissor-type cutting action.

Item 21: The retinaculatome of any other item, wherein the surgical blade comprises a movable sharp blade surface that provides a cutting action in combination with another surface.

Item 22: The retinaculatome of any other item, wherein a distal end surface of the sleeve exterior shell is substantially transparent.

Item 23: The retinaculatome of any other item, wherein the sleeve exterior shell is substantially transparent.

Item 24: The retinaculatome of any other item, wherein the sleeve exterior shell comprises plastic, metal and/or glass material that is sterile.

Item 25: The retinaculatome of any other item, wherein the incision imaging window comprises plastic and/or glass material that is compatible with sterilization and is substantially transparent.

Item 26: The retinaculatome of any other item, wherein the lower guide plate comprises plastic, metal and/or glass material that is sterile.

Item 27: The retinaculatome of any other item, further comprising an extension sheath connected to the sleeve exterior shell at the sleeve proximal end.

Item 28: A method of transecting a flexor retinaculum in a carpal tunnel release surgery using a retinaculatome, the method comprising:

inserting a borescope into a sleeve interior cavity of a sterile borescope sleeve of the retinaculatome, wherein a sleeve distal end has an incision imaging window transparent to the sleeve interior cavity;

positioning a surgical blade in a mounted blade position defined by a surgical blade mount connected to a lower guide plate extending from the sleeve distal end;

positioning the retinaculatome within a surgical incision such that the lower guide plate defines a horizontal surgical travel direction; and transecting the flexor retinaculum by advancing the surgical blade along the horizontal surgical travel direction while viewing through the incision imaging window using the borescope.

Item 29: The method of any other item, wherein the sterile borescope sleeve comprises a sleeve exterior shell that is sealed along its length and sealed at the sleeve distal end.

Item 30: The method of any other item, wherein the mounted blade position overlies the lower guide plate.

Item 31: The method of any other item, wherein the borescope is non-sterile.

Item 32: The method of any other item, further comprising disposing of the sterile borescope sleeve after the carpal tunnel release surgery while retaining the borescope for reuse.

Item 33: The method of any other item, wherein the borescope is a wireless borescope and a sleeve proximal end is closed after insertion of the borescope.

Item 34: The method of any other item, wherein the borescope includes a non-sterile borescope cable and the method further comprises connecting an extension sheath at a proximal end of the sterile borescope sleeve to enclose a distal portion of the non-sterile borescope cable.

Item 35: The method of any other item, wherein the borescope is positioned within the sleeve interior cavity to have a downward viewing angle of 0-45° relative to the horizontal surgical travel direction.

Item 36: The method of any other item, further comprising shielding the mounted blade position using a tissue shield extending from the sleeve distal end and vertically spaced above the lower guide plate.

Item 37: The method of any other item, wherein the sleeve exterior shell is substantially transparent.

Item 38: The method of any other item, wherein the flexor retinaculum is transected using a fixed and straight cutting edge of the surgical blade.

Item 39: The method of any other item, wherein the flexor retinaculum is transected using a fixed and curved cutting edge of the surgical blade.

Item 40: The method of any other item, wherein the flexor retinaculum is transected using a scissor-type cutting action.

Item 41: The method of any other item, wherein a distal end of the lower guide plate is arcuate.

Item 42: The method of any other item, wherein a lower guide plate width is substantially constant between a lower guide plate proximal end and a lower guide plate distal end.

Item 43: The method of any other item, wherein a lower guide plate width decreases gradually between a lower guide plate proximal end and a lower guide plate distal end.

Item 44: The method of any other item, wherein the tissue shield is dome-shaped.

Item 45: The method of any other item, wherein a distal end of the tissue shield is arcuate.

Item 46: The method of any other item, wherein a tissue shield width is substantially constant between a tissue shield proximal end and a tissue shield distal end.

Item 47: The method of any other item, wherein a tissue shield width decreases gradually between a tissue shield proximal end and a tissue shield distal end.

Item 48: The method of any other item, wherein a sleeve length between a sleeve proximal end and the sleeve distal end is at least 3 cm.

Item 49: The method of any other item, wherein the sleeve exterior shell comprises plastic, metal and/or glass material that is sterile.

The invention claimed is:

1. A method of transecting a flexor retinaculum in a carpal tunnel release surgery using a retinaculatome, the method comprising:

inserting a borescope into a sleeve interior cavity of a sterile borescope sleeve of the retinaculatome, the sterile borescope sleeve comprising a sleeve exterior shell that is sealed along its length and sealed at a sleeve distal end, wherein the sleeve distal end has an incision imaging window transparent to the sleeve interior cavity;

positioning a surgical blade in a mounted blade position defined by a surgical blade mount connected to a lower guide plate extending from the sleeve distal end, the mounted blade position overlying the lower guide plate;

positioning the retinaculatome within a surgical incision such that the lower guide plate defines a horizontal surgical travel direction; and transecting the flexor retinaculum by advancing the surgical blade along the horizontal surgical travel direction while viewing through the incision imaging window using the borescope.

2. The method of claim 1, wherein the borescope is non-sterile.

3. The method of claim 1, further comprising disposing of the sterile borescope sleeve after the carpal tunnel release surgery while retaining the borescope for reuse.

4. The method of claim 1, wherein the borescope is a wireless borescope and a sleeve proximal end is closed after insertion of the borescope.

5. The method of claim 1, wherein the borescope includes a non-sterile borescope cable and the method further comprises connecting an extension sheath at a proximal end of the sterile borescope sleeve to enclose a distal portion of the non-sterile borescope cable.

6. The method of claim 1, wherein the borescope is positioned within the sleeve interior cavity to have a downward viewing angle of 0-45° relative to the horizontal surgical travel direction.

7. The method of claim 1, further comprising shielding the mounted blade position using a tissue shield extending from the sleeve distal end and vertically spaced above the lower guide plate.

8. The method of claim 7, wherein the tissue shield is dome-shaped.

9. The method of claim 7, wherein a distal end of the tissue shield is arcuate.

10. The method of claim 7, wherein a tissue shield width is substantially constant between a tissue shield proximal end and a tissue shield distal end.

11. The method of claim 7, wherein a tissue shield width decreases gradually between a tissue shield proximal end and a tissue shield distal end.

12. The method of claim 1, wherein the sleeve exterior shell is substantially transparent.

13. The method of claim 1, wherein the flexor retinaculum is transected using a fixed and straight cutting edge of the surgical blade.

14. The method of claim 1, wherein the flexor retinaculum is transected using a fixed and curved cutting edge of the surgical blade.

15. The method of claim 1, wherein the flexor retinaculum is transected using a scissor-type cutting action.

16. The method of claim 1, wherein a distal end of the lower guide plate is arcuate.

17. The method of claim 1, wherein a lower guide plate width is substantially constant between a lower guide plate proximal end and a lower guide plate distal end.

18. The method of claim 1, wherein a lower guide plate width decreases gradually between a lower guide plate proximal end and a lower guide plate distal end.

19. The method of claim 1, wherein a sleeve length between a sleeve proximal end and the sleeve distal end is at least 3 cm.

20. The method of claim 1, wherein the sleeve exterior shell comprises plastic, metal and/or glass material that is sterile.

* * * * *